(12) United States Patent  
Werner et al.

(10) Patent No.: US 10,596,417 B2  
(45) Date of Patent: Mar. 24, 2020

(54) FITNESS ACTIVITY MONITORING SYSTEMS AND METHODS

(71) Applicant: adidas AG, Herzogenaurach (DE)

(72) Inventors: Jon Harald Werner, Austin, TX (US); Christian Dibenedetto, Northplains, OR (US); Stephen John Black, Portland, OR (US)

(73) Assignee: adidas AG, Herzogenaurach (DE)

( * ) Notice: Subject to any disclaimer, the term of this patent is extended or adjusted under 35 U.S.C. 154(b) by 37 days.

(21) Appl. No.: 15/793,067

(22) Filed: Oct. 25, 2017

(65) Prior Publication Data

US 2018/0085628 A1   Mar. 29, 2018

Related U.S. Application Data

(63) Continuation of application No. 15/184,638, filed on Jun. 16, 2016, now Pat. No. 9,814,937, which is a (Continued)

(51) Int. Cl.  
*G09G 5/00* (2006.01)  
*A63B 24/00* (2006.01)  
(Continued)

(52) U.S. Cl.  
CPC ...... *A63B 24/0062* (2013.01); *A63B 24/0021* (2013.01); *G01S 5/0257* (2013.01); (Continued)

(58) Field of Classification Search  
CPC ............ A63B 24/0021; A63B 24/0062; A63B 2220/12; A63B 2220/14; (Continued)

(56) References Cited

U.S. PATENT DOCUMENTS

| | | |
|---|---|---|
| 6,768,944 B2 | 7/2004 | Breed et al. |
| 7,085,637 B2 | 8/2006 | Breed et al. |

(Continued)

FOREIGN PATENT DOCUMENTS

| | | |
|---|---|---|
| CN | 101689304 A | 3/2010 |
| CN | 101713660 A | 5/2010 |

(Continued)

OTHER PUBLICATIONS

European Search Report for Application No. EP 12198417, dated May 29, 2013, 4 pages.

*Primary Examiner* — Lawrence S Galks  
(74) *Attorney, Agent, or Firm* — Sterne, Kessler, Goldstein & Fox P.L.L.C.

(57) ABSTRACT

Apparatus, systems, and methods for monitoring the performance of an individual during a fitness activity are disclosed. A method of monitoring the performance of a participant engaged in a fitness activity includes receiving a GPS signal during the fitness activity at a portable fitness device used by the participant; determining participant performance data based on the received GPS signal; at a stationary position beacon, transmitting location data associated with the location of the stationary position beacon; at a mobile participant receiver supported by the participant, receiving the location data from the stationary position beacon; and modifying the participant performance data based on the data received from the stationary position beacon.

22 Claims, 10 Drawing Sheets

Related U.S. Application Data continuation of application No. 13/335,629, filed on Dec. 22, 2011, now Pat. No. 9,424,397.

(51) Int. Cl.
*G06F 19/00* (2018.01)
*G01S 5/02* (2010.01)
*G01S 19/19* (2010.01)
*G01S 19/48* (2010.01)

(52) U.S. Cl.
CPC .............. *G01S 19/19* (2013.01); *G01S 19/48* (2013.01); *G06F 19/3481* (2013.01); *A63B 2024/0025* (2013.01); *A63B 2220/12* (2013.01); *A63B 2220/14* (2013.01); *A63B 2220/20* (2013.01); *A63B 2220/30* (2013.01); *A63B 2225/54* (2013.01)

(58) Field of Classification Search
CPC ... A63B 2024/0025; A63B 2071/0691; H04W 4/0008; H04W 4/02; H04W 4/021; H04W 4/023; H04W 4/027; H04W 64/00; G01S 19/07; G01S 19/19; G01S 19/48; G01S 5/0257; G01C 21/20
See application file for complete search history.

(56) References Cited

U.S. PATENT DOCUMENTS

| | | | |
|---|---|---|---|
| 7,171,331 B2 | 1/2007 | Vock et al. | |
| 7,174,277 B2 | 2/2007 | Vock et al. | |
| 7,254,516 B2 | 8/2007 | Case, Jr. et al. | |
| 7,292,867 B2 | 11/2007 | Werner et al. | |
| 7,353,136 B2 | 4/2008 | Vock et al. | |
| 7,353,137 B2 | 4/2008 | Vock et al. | |
| 7,480,512 B2 | 1/2009 | Graham et al. | |
| 7,579,946 B2 | 8/2009 | Case, Jr. | |
| 7,603,255 B2 | 10/2009 | Case, Jr. et al. | |
| 7,607,243 B2 | 10/2009 | Berner, Jr. et al. | |
| 7,620,520 B2 | 11/2009 | Vock et al. | |
| 7,627,451 B2 | 12/2009 | Vock et al. | |
| 7,706,815 B2 | 4/2010 | Graham et al. | |
| 7,805,149 B2 | 9/2010 | Werner et al. | |
| 7,805,150 B2 | 9/2010 | Graham et al. | |
| 7,941,160 B2 | 5/2011 | Werner et al. | |
| 7,953,549 B2 | 5/2011 | Graham et al. | |
| 7,957,752 B2 | 6/2011 | Werner et al. | |
| 7,969,314 B2 | 6/2011 | Boyd et al. | |
| 8,015,732 B2 | 9/2011 | Berner, Jr. et al. | |
| 8,028,443 B2 | 10/2011 | Case, Jr. | |
| 8,060,308 B2 | 11/2011 | Breed | |
| 8,068,858 B2 | 11/2011 | Werner et al. | |
| 8,068,979 B2 | 11/2011 | Breed | |
| 8,086,421 B2 | 12/2011 | Case, Jr. et al. | |
| 8,112,251 B2 | 2/2012 | Case, Jr. et al. | |
| 8,188,868 B2 | 5/2012 | Case, Jr. | |
| 8,209,120 B2 | 6/2012 | Breed | |
| 8,224,429 B2 | 7/2012 | Prstojevich et al. | |
| 8,244,226 B2 | 8/2012 | Werner et al. | |
| 8,244,278 B2 | 8/2012 | Werner et al. | |
| 8,248,247 B2 | 8/2012 | Boyd et al. | |
| 8,255,144 B2 | 8/2012 | Breed et al. | |
| 8,258,941 B2 | 9/2012 | Case, Jr. | |
| 8,260,537 B2 | 9/2012 | Breed | |
| 8,260,667 B2 | 9/2012 | Graham et al. | |
| 8,280,681 B2 | 10/2012 | Vock et al. | |
| 8,350,708 B2 | 1/2013 | Case, Jr. | |
| 9,409,052 B2 | 8/2016 | Werner | |
| 2002/0177476 A1* | 11/2002 | Chou | G01S 5/0027 455/574 |
| 2005/0227811 A1 | 10/2005 | Shum et al. | |
| 2006/0143645 A1* | 6/2006 | Vock | A43B 3/00 725/9 |
| 2007/0006489 A1 | 1/2007 | Case, Jr. et al. | |
| 2007/0159926 A1 | 7/2007 | Prstojevich et al. | |
| 2007/0247306 A1 | 10/2007 | Case | |
| 2008/0082254 A1 | 4/2008 | Huhtala | |
| 2008/0258917 A1* | 10/2008 | Boyd | A63B 24/0062 340/572.1 |
| 2009/0009398 A1 | 1/2009 | Taylor | |
| 2009/0075677 A1* | 3/2009 | Seger | G08B 21/0261 455/456.6 |
| 2009/0228157 A1 | 9/2009 | Breed | |
| 2010/0088023 A1* | 4/2010 | Werner | A63B 24/0021 701/467 |
| 2010/0205242 A1* | 8/2010 | Marchioro, II | G06Q 10/10 709/203 |
| 2011/0029611 A1 | 2/2011 | Hutchison et al. | |
| 2011/0196603 A1 | 8/2011 | Graham et al. | |
| 2011/0238755 A1 | 9/2011 | Khan et al. | |
| 2011/0250937 A1 | 10/2011 | Hubbard et al. | |
| 2011/0314700 A1 | 12/2011 | Case, Jr. et al. | |
| 2011/0314702 A1 | 12/2011 | Berner, Jr. et al. | |
| 2012/0004956 A1* | 1/2012 | Huston | H04W 4/21 705/14.1 |
| 2012/0035487 A1 | 2/2012 | Werner et al. | |
| 2012/0041767 A1 | 2/2012 | Hoffman et al. | |
| 2012/0078396 A1 | 3/2012 | Case, Jr. et al. | |
| 2012/0136689 A1 | 5/2012 | Ickman et al. | |
| 2012/0265326 A1 | 10/2012 | Prstojevich et al. | |
| 2012/0293326 A1 | 11/2012 | Case, Jr. | |
| 2012/0299725 A1 | 11/2012 | Boyd et al. | |
| 2012/0303753 A1 | 11/2012 | Hansen | |
| 2012/0306907 A1* | 12/2012 | Huston | G06K 9/00671 345/619 |
| 2013/0030931 A1 | 1/2013 | Moshfeghi | |
| 2013/0166048 A1 | 6/2013 | Werner et al. | |

FOREIGN PATENT DOCUMENTS

| | | |
|---|---|---|
| CN | 101890215 A | 11/2010 |
| CN | 102037375 A | 4/2011 |
| CN | 201906448 U | 7/2011 |
| DE | 102007040602 | 3/2009 |
| EP | 2 172 249 A2 | 4/2010 |
| JP | 2001-188805 A | 7/2001 |
| JP | 2006-271611 A | 10/2006 |
| JP | 2010-532673 A | 10/2010 |

* cited by examiner

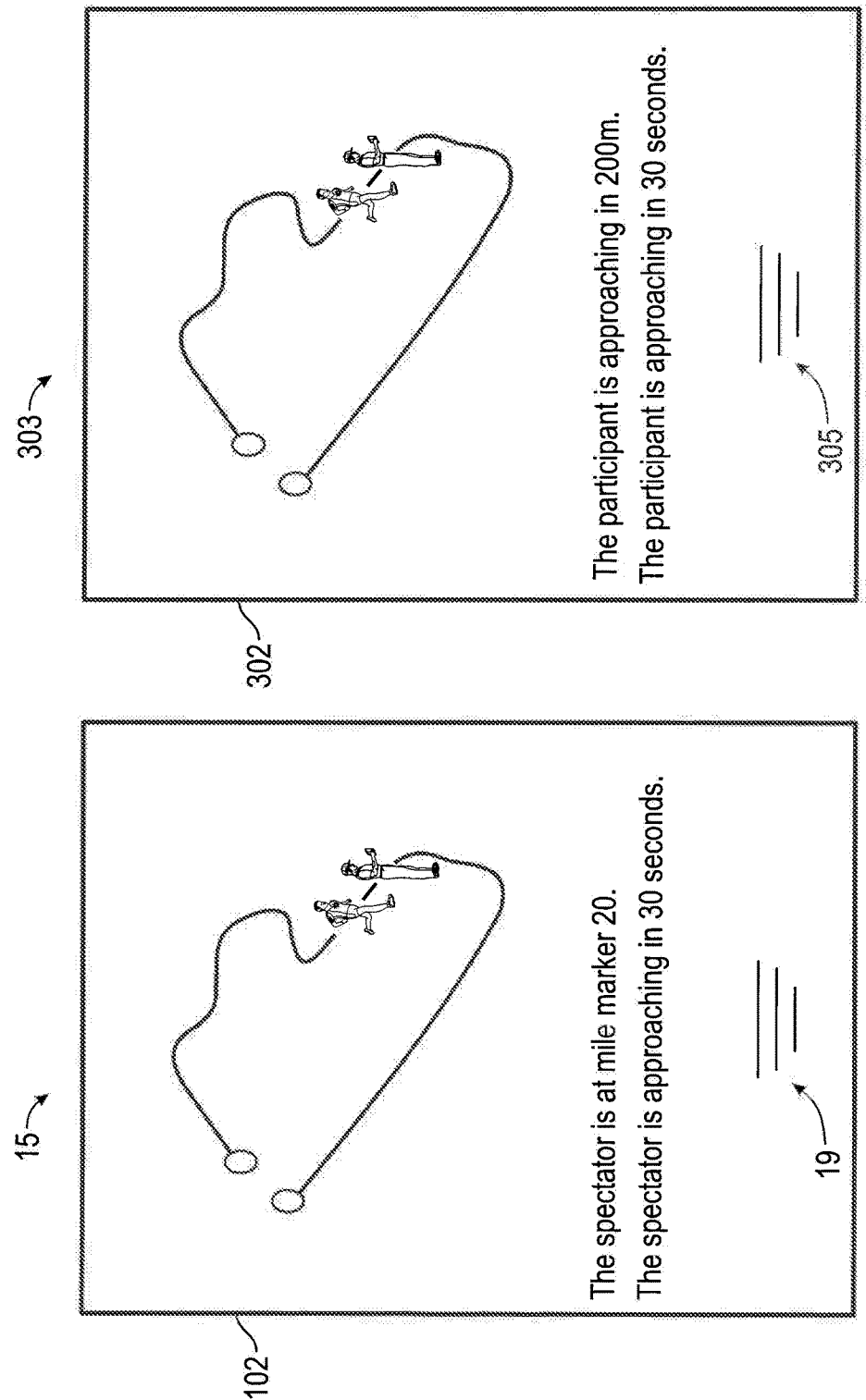

FITNESS ACTIVITY MONITORING SYSTEMS AND METHODS

CROSS-REFERENCE TO RELATED APPLICATION

This application is a continuation of U.S. patent application Ser. No. 15/184,638, filed Jun. 16, 2016, which is a continuation of U.S. patent application Ser. No. 13/335,629, filed Dec. 22, 2011, both of which are incorporated herein in their entireties by reference thereto.

BACKGROUND OF THE INVENTION

Field of the Invention

The present invention is directed to fitness activity monitoring. More particularly, embodiments of the present invention are directed to systems and methods for monitoring the performance of a fitness activity participant.

Background Art

Participation in fitness activities, such as a competitive racing event, can be important for maintaining a healthy lifestyle and individual well-being. Technology has resulted in the development of systems capable of monitoring information about the individuals engaged in these activities. For example, some competitive race events include chip timing systems that may monitor the location of a participant during the race. These systems, however, may be limited to only providing location and timing information at certain points along the race course. Moreover, these systems may not be capable of providing other performance information to the participant during the race, such as, pace, speed, and distance, for example. Fitness monitoring systems and methods are needed that provide accurate real-time information to participants of these activities. Providing racing participants with accurate real-time information and performance data can enable an athlete to better control his performance and adapt the performance over the course of the race in order to ideally spend the available resources. In addition, those that watch fitness activities may enjoy the excitement of the competition and may wish to monitor the performance of one or more participants. Monitoring the performance of a racing participant is not only useful from an entertainment perspective, but can, for example, provide a comparison of the physical performances of different participants. Moreover, monitored performance data may be used for supervising the physical condition of an athlete (e.g., by medical staff) in order to prevent injuries or other health threats.

BRIEF SUMMARY OF THE INVENTION

Embodiments of the present invention relate to a method of monitoring the performance of a participant engaged in a fitness activity, comprising: receiving a GPS signal during the fitness activity at a portable fitness device used by the participant; determining participant performance data based on the received GPS signal; at a stationary position beacon, transmitting location data associated with the location of the stationary position beacon; at a mobile participant transceiver supported by the participant, receiving the location data from the stationary position beacon; and modifying the participant performance data based on the data received from the stationary position beacon. The steps of the method may be executed using at least one processor, provided on the portable fitness device, the mobile participant transceiver, the position beacon, and/or a remote server, for example.

In another embodiment, a method of monitoring the performance of a participant engaged in a competitive race having a predetermined route, comprises: determining participant performance data based on a GPS signal received by a portable fitness device used by the participant during the race; from a stationary position beacon positioned at a predetermined location along the route, transmitting location data associated with the location of the stationary position beacon; at a mobile participant transceiver supported by the participant, receiving the location data from the stationary position beacon; and modifying the participant performance data based on the data received from the stationary position beacon. The steps of the method may be executed using at least one processor, provided on the portable fitness device, the mobile participant transceiver, the position beacon, and/or a remote server, for example.

In another embodiment, a system for monitoring the performance of a participant engaged in a competitive race having a predetermined route, comprises: a plurality of stationary position beacons positioned at predetermined locations along the route each transmitter wirelessly transmitting location data associated with the race; and a portable fitness device used by the participant during the race for determining participant performance data based on a GPS signal received by the portable fitness device and modifying the performance data based at least on the transmitter location data. The methods described herein may be implemented in any combination of hardware and/or software, i.e., computer programs.

In another embodiment, a computer-implemented method of monitoring the performance of a participant engaged in a fitness activity, preferably a race, includes: receiving a GPS signal during the fitness activity at a portable fitness device used by the participant; determining participant performance data based on the received GPS signal; from a stationary position beacon, receiving location data associated with the location of the stationary position beacon; and modifying the participant performance data based on the data received from the stationary position beacon.

Embodiments of the present invention may include one or more features described in commonly owned U.S. Publication No. 2011/0082641, entitled "Methods and Computer Program Products for Providing Information About a User During a Physical Activity," U.S. patent application Ser. No. 12/836,421, filed Jul. 14, 2010 and entitled "Fitness Monitoring Methods, Systems and Program Products, and Applications Thereof," and U.S. patent application Ser. No. 12/836,416, filed Jul. 14, 2010 and entitled "Location-Aware Fitness Monitoring Methods, Systems, and Program Products, and Applications Thereof," the disclosures of which are hereby incorporated in their entirety by reference thereto.

BRIEF DESCRIPTION OF THE DRAWINGS

The accompanying drawings, which are incorporated herein and form a part of the specification, illustrate the present invention and, together with the description, further serve to explain the principles of the invention and to enable a person skilled in the pertinent art to make and use the invention.

FIG. 9 is a schematic diagram of a fitness monitoring device display depicting an alert based corrected participant performance data according to an embodiment of the present invention.

FIG. 10 is a schematic diagram of a spectator device display depicting an alert based corrected participant performance data according to an embodiment of the present invention.

DETAILED DESCRIPTION OF THE INVENTION

Figure 1:
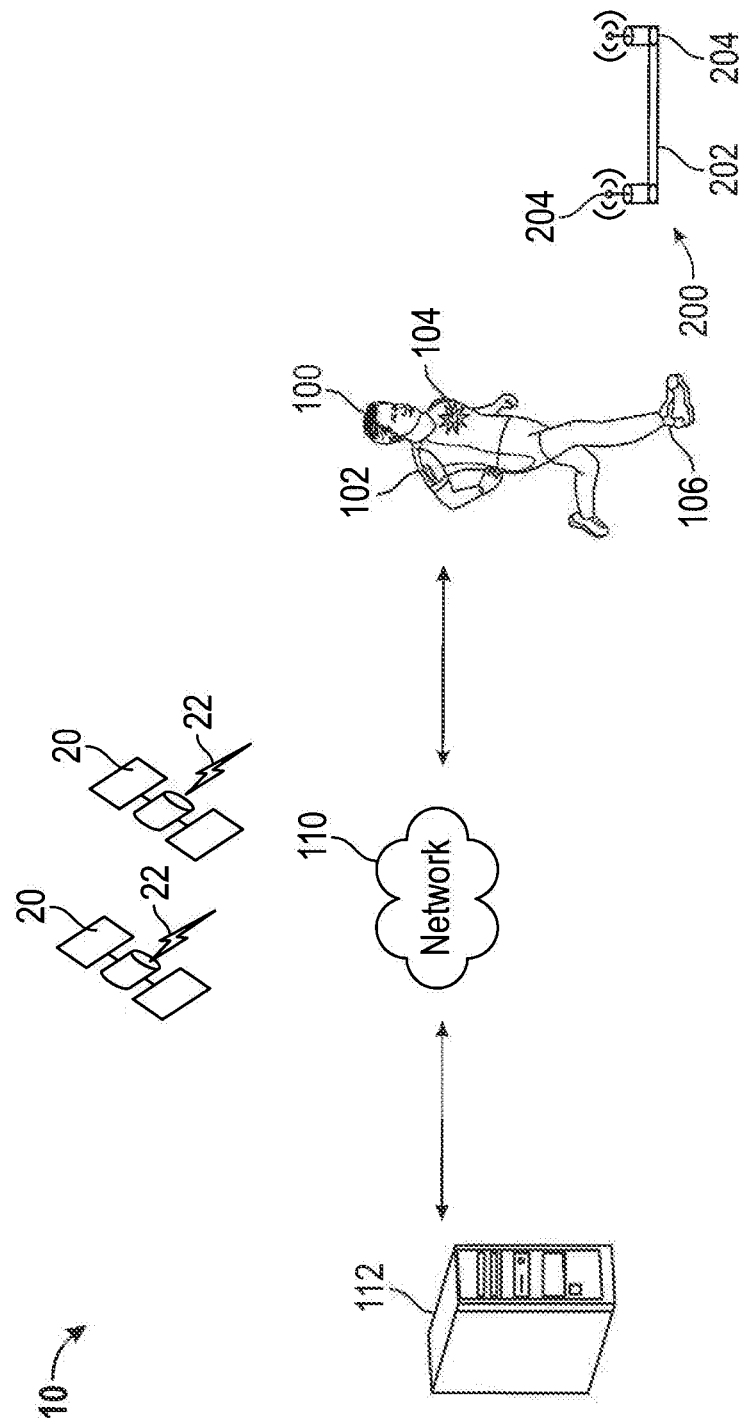
FIG. 1 is a schematic diagram of a fitness activity monitoring system including a stationary position beacon according to an embodiment of the present invention.

The present invention will now be described in detail with reference to embodiments thereof as illustrated in the accompanying drawings, in which like reference numerals are used to indicate identical or functionally similar elements. References to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The following examples are illustrative, but not limiting, of the present invention. Other suitable modifications and adaptations of the variety of conditions and parameters normally encountered in the field, and which would be apparent to those skilled in the art, are within the spirit and scope of the invention.

Embodiments of the present invention include a system 10 for monitoring the performance of one or more individuals during a fitness activity. As discussed below, the fitness activity includes a predetermined route (e.g., a race course) to be traversed by the participant during the fitness activity. In various embodiments, the present invention includes a system 10 for monitoring the performance of a participant (e.g., an athlete) 100 engaged in the fitness activity. With reference to FIG. 1, the system includes a portable fitness monitoring device 102 used by the fitness activity participant 100 and adapted to determine and/or transmit real-time performance data associated with the participant during the fitness activity. The performance data may include location, pace, speed, distance, and other data associated with the participant's performance during the fitness activity. The portable fitness monitoring device 102 is in communication with a fitness activity server 112 over a network 110 and may communicate the performance data of the participant 100 to the server 112. As will be appreciated, in an embodiment, the network 110 may be the internet, a Bluetooth network, GSM, WLAN, WAN, or other suitable communication network. In an alternate embodiment, the network may be a private network or intranet, such as, for example, a network dedicated to a particular fitness activity (e.g., the New York City Marathon). Other suitable communication networks may be used. In some embodiments, the performance data may be communicated and/or received after completion of the fitness activity.

The system 10 further includes a position beacon system 200 disposed at predetermined distances along the predetermined route. The position beacon system 200 is directly or indirectly in communication with the portable fitness monitoring device 102 and/or the fitness activity server 112 and transmits a signal associated with its predetermined location along the route. In one embodiment, the signal includes time-stamped location information that indicates the location of the beacon system 200 and the time at which the signal was transmitted such that participant performance data (e.g., location, speed, pace, distance) may be precisely determined either alone or in conjunction with additional data. For example, the beacon signal information may be used in conjunction with GPS data acquired by the portable fitness device 102. In one embodiment, after receiving the beacon signal, the system 10 modifies participant performance data based at least on the beacon signal information. In this manner, in one embodiment the monitoring system 10 may provide more accurate participant performance data during the fitness activity, including participant location, than which data may be provided by the portable fitness monitoring device 102 alone.

As will be appreciated by one of ordinary skill in the art, the portable fitness monitoring device 102 may be a device such as, for example, a mobile phone, a smartphone, a personal digital assistant, a music file player (e.g. an MP3 player), a tablet computer, a laptop computer, an intelligent article for wearing (e.g. a fitness monitoring garment, wrist band, or watch), a dongle (e.g. a small hardware device that is capable of physically coupling to a first electronic device and/or wirelessly coupling to additional electronic devices), or any other suitable device dedicated or non-dedicated to providing the monitoring methods described herein. The device may be supported by the participant 100 such that it may be easily used while engaged in the fitness activity. In one embodiment, the device may be mounted to the body of the participant 100. For example, the device may be arm-mounted, chest-mounted, leg-mounted, or foot-mounted. In one embodiment, portable fitness monitoring device 102 may be hand held.

In one embodiment, as shown, for example, in FIG. 1, the portable fitness monitoring device 102 comprises a global positioning system (GPS) equipped device. The system 10 may include GPS satellites 20 that continuously emit GPS signals 22 which may allow the portable fitness monitoring device 102 to continuously determine its location, speed, pace, distance traveled, bearing, and similar performance data according to known techniques. As will be appreciated, the fitness monitoring device 102 includes the necessary GPS receiver/transmitter to receive and transmit participant performance data. The portable fitness monitoring device 102 may continuously transmit performance data to the server 112 or other device (e.g., a spectator device, as described below), or may transmit at a predetermined interval for power saving purposes.

The portable fitness device 102 may also be adapted to measure or receive data regarding various performance parameters associated with the participant's performance during the fitness activity. As shown in FIG. 1, in one embodiment the system 10 may include one or more additional sensors 104 and 106 for measuring performance parameters of the participant 100. For example, the system 10 may include a heart rate sensor 104 for determining heart rate information during the fitness activity, and an accelerometer 106. In one embodiment, the accelerometer 106 may be used in conjunction with a GPS-enabled portable fitness monitoring device 102 to determine the location of the participant 100 according to known techniques. For example, data provided by the accelerometer 106 may be used to provide a "dead reckoning" of the participant's location when the GPS signal is interrupted (e.g., due to the participant traversing the route under a bridge). The system 10 may include other sensors including, but not limited to, a pedometer, pulsimeter, breath rate sensor, gyroscope, magnetometer, hydration sensor, thermometers, or other suitable sensors for detecting information that may be used to measure and/or calculate performance parameters. Each of the sensors of the system 10 may be in communication with the portable fitness monitoring device 102 in a wireless and/or wireless connection and may provide performance data regarding the participant 100 during the fitness activity. In one embodiment, the performance data may be transmitted from the portable fitness monitoring device 102 to the server 112 and/or another device (e.g., a spectator device, as described below) over the network 110. In some embodiments the performance data is stored on the portable fitness monitoring device 102.

The fitness activity may include any fitness activity engaged in by the participant 100 and including the position beacon system 200. In one embodiment, the fitness activity is a competitive fitness activity, including, but not limited to, a foot race, a bicycle race, a skiing or snowboarding race, or other fitness activity in which the physical location of the participant 100 changes as a function of time. The fitness activity may be of any desired length and may be a timed event. For example, the fitness activity may comprise an organized competitive running race such as the New York City Marathon, the Army Ten Miler in Washington, D.C., or a 5K high school cross-country race. In an embodiment, the fitness activity may be a self-organized activity. For example, a participant may organize a fitness activity to be engaged in with one or more individuals, such as family, friends, or members of a social network. The social network may include Facebook® friends, LinkedIn® contacts, Twitter® followers, members of a athlete community on a fitness website, and the like. In one embodiment, the fitness activity includes a predetermined route to be traversed by one or more participants. The predetermined route may be provided by a race organizer, for example, as would be the case for a competitive running race like the New York City Marathon. In some embodiments, the predetermined route may comprise a route created and scheduled by the participant. For example, the predetermined route may be created and scheduled according to embodiments described in U.S. Publication No. 2011/0082641, entitled "Methods and Computer Program Products for Providing Information About a User During a Physical Activity." In one embodiment, the predetermined route may be created and scheduled, for example, to be a 5K race that takes place every Wednesday at the same location and time, and may be saved in the user's account on server 112. The server 112 may store information related to the fitness activity, including the predetermined route of the fitness activity, which may be downloaded to the portable fitness monitoring device 102. In some embodiments, the fitness activity may comprise a vehicle race, such as, for example, a car or boat race.

With renewed reference to FIG. 1, in one embodiment the position beacon system 200 includes a plurality of race mats 202. Each mat 202 may be a substantially flat member disposed along the ground of the route of the fitness activity at a predetermined location. The mat 202 may include one or more antennae or transmitters 204 for transmitting unique location and timing information associated with the position of the particular mat 202. The transmitters 204 are adapted to transmit the signal using known technologies including, but not limited to, RFID, Bluetooth, magnetic field, near field communication systems, or other suitable technologies adapted to provide a signal that includes time-stamped location information. In one embodiment, the transmitters 204 may include a receiver and be adapted to transmit and receive data. In one embodiment, the one or more transmitters 204 may be embedded in the mat 202 or may be disposed on the mat 202. The mat 202 is preferably sized and shaped to accommodate the traversal of a plurality of participants 100 during the fitness activity. For example, the mat 202 may stretch across the width of a road used in a race course, and may have a substantially low height profile so as not to interfere with the gait of the race participants. During a fitness activity, each mat 202 transmits a signal that includes time-stamped location information. When the participant 100 is proximate to the mat 202 (e.g., as the participant 100 crosses over the mat), the signal is received by the portable fitness monitoring device 102. The portable fitness monitoring device 102 may also receive location data from the GPS signal 22 from GPS satellites 20. Based at least on the position beacon system 200 signal, the precise location of the participant may be determined.

Figure 2:
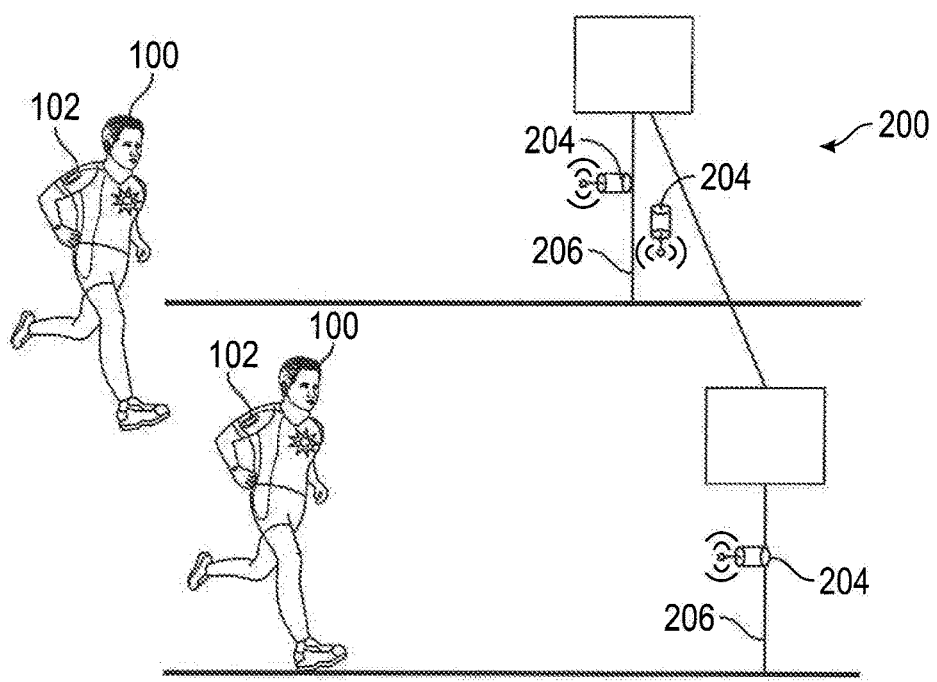
FIG. 2 is a schematic diagram of a stationary position beacon system according to an embodiment of the present invention.

With reference to FIG. 2, in one embodiment, the position beacon system 200 includes a tower 206 and one or more transmitters 204 connected thereto that may be used in addition to, or instead of, mat 202. The transmitters 204 may be provided in a side arrangement and/or an overhead arrangement, as shown, in order to transmit the signal such that it may be received either directly or indirectly at the portable fitness monitoring device 102. As will be appreciated by those of ordinary skill in the art, the position beacon system 200 may be positioned such that the signal is received by the portable fitness monitoring device 102 when the participant is proximate to the system 200. For example, the signal may be received when the participant 200 is on top of the mat 202, next to the tower 206, under the tower 206 or otherwise proximate to the system 200. Other suitable embodiments of a position beacon system 200, including systems that do not include a mat 202 or a tower 206 as an antenna support structure, may be used to transmit a unique time-stamped location signal to the participant 200 along the predetermined route of the fitness activity. In one embodiment, the position beacon system 200 may include light barrier or magnetic field technology.

Figure 3:
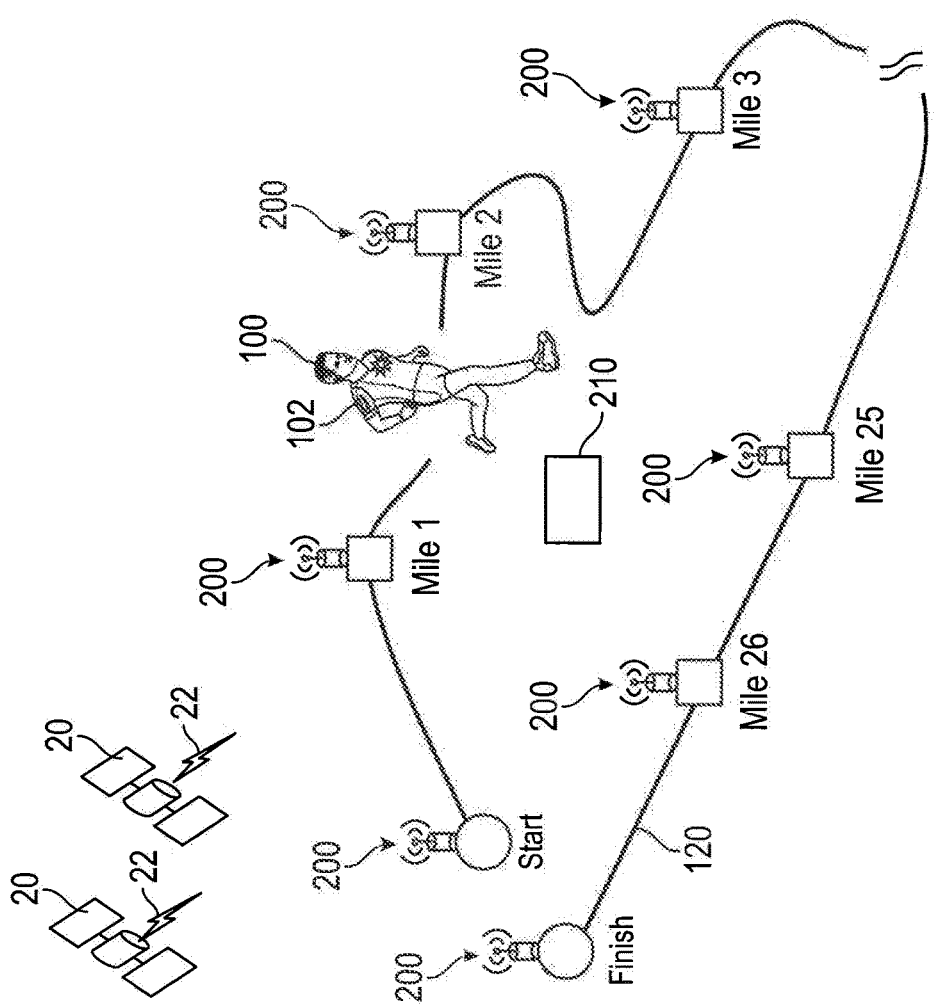
FIG. 3 is a schematic view of a stationary position beacon system along a race course according to an embodiment of the present invention.

As shown in FIG. 3, the position beacon system 200 including a plurality of time-stamped location signal transmitters (such as, for example, on a plurality of mats 202 or other suitable position beacon support structures, such as, for example, towers 206) are disposed at predetermined distances along a route 120 of the fitness activity (e.g., a race course). For a competitive race, for example, mats 202 may be placed at the race start line and finish line and at predetermined positions intermediate to the start line and finish line. By way of further example, in a marathon, mats 202 may be placed at each mile marker along the route 120 of the race, as shown schematically in FIG. 3. Mats 202 may be provided at other locations including, but not limited to, aid stations, water stations, and race course landmarks. In one embodiment, the position beacon system 200 may be provided by a race organizer, for example, as may be the case for a competitive running race like the New York City Marathon. As shown in FIG. 3, the portable fitness monitoring device 102 may receive a GPS signal 22 from GPS satellite 20. The portable fitness monitoring device 102 may directly or indirectly interact with the position beacon system 200 to receive location and/or timing data from the transmitter 204 and modify participant performance data accordingly to provide more accurate data.

In one embodiment, the position beacon system 200 may include a controller 210, as shown in FIG. 3. The controller 210 may be in communication with the mats 202 and may provide timing and other race data to the mats 202 for transmission to the participants 200. For example, the controller 210 may include an official race clock on which timing calculations may be based. In one embodiment, the controller 210 may be centrally located on the race course 120 so as to efficiently communicate with the mats 202. In one embodiment, multiple controllers 210 may be used. The controller 210 may be administered by a race organizer, for example.

Figure 4:
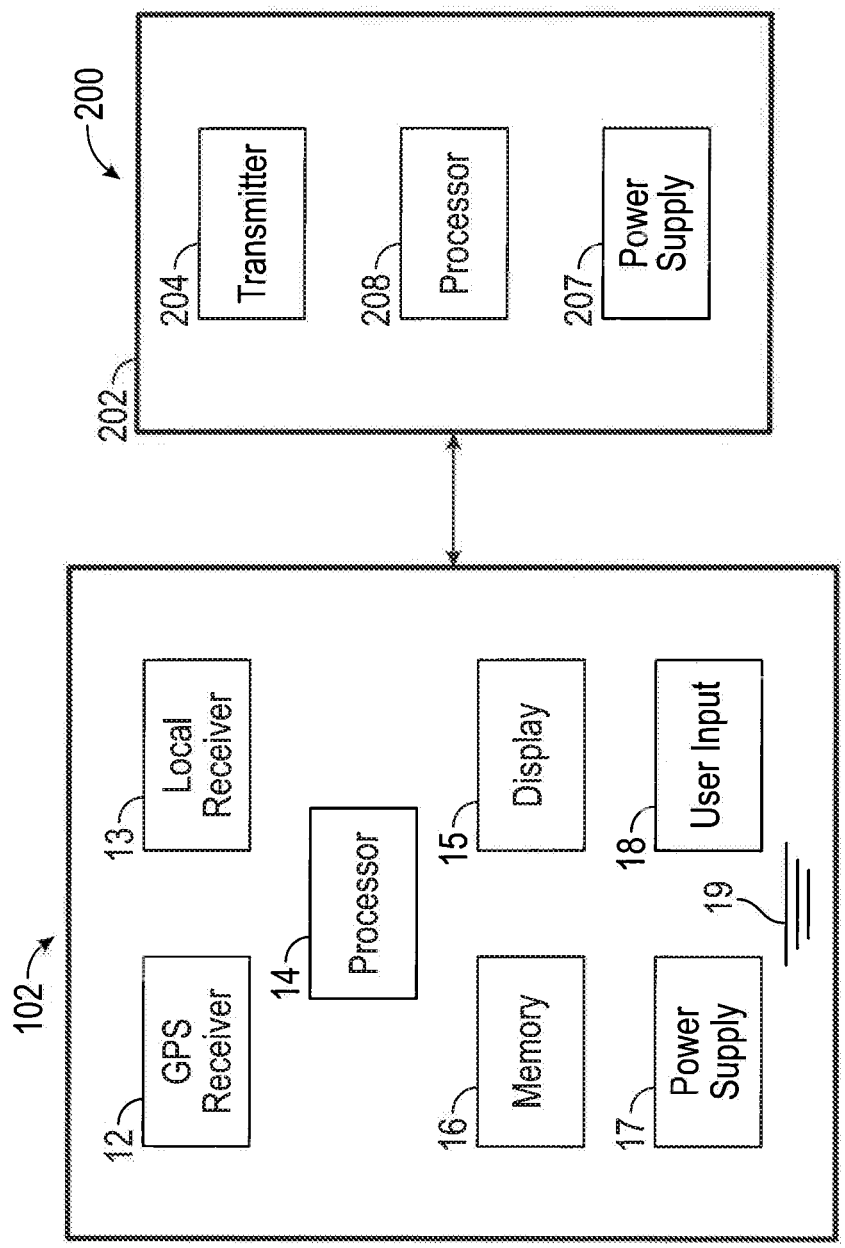
FIG. 4 is a block diagram of fitness monitoring system according to an embodiment of the present invention.
Figure 5:
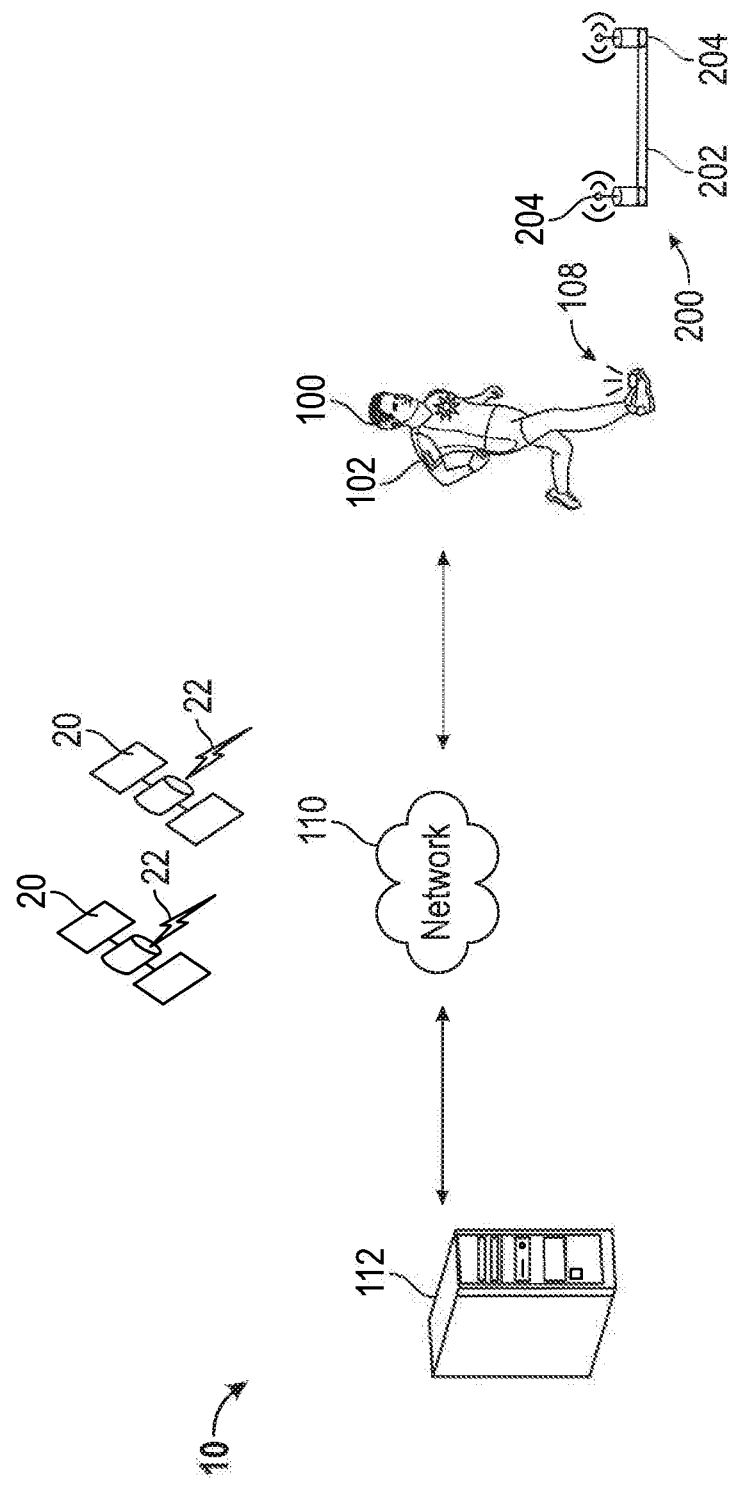
FIG. 5 is a schematic diagram of a fitness activity monitoring system including a separate mobile participant transceiver according to an embodiment of the present invention.

As shown in FIG. 4, the portable fitness monitoring device 102 and the position beacon system 200 are adapted to communicate to provide the fitness monitoring methods of the present invention. In one exemplary embodiment, the portable fitness monitoring device 102 includes a GPS receiver 12 for receiving GPS signals 22 from satellites 20. In some embodiments, receiver 12 may be a transceiver adapted to receive and transmit data. Using the GPS signal data, a processor 14 calculates participant performance data (e.g., location, speed, pace, and distance). The portable fitness monitoring device 102 then transmits participant performance data to server 112 and/or other devices within the monitoring system 10 over network 110. For example, as will be appreciated, in embodiments in which the portable fitness monitoring device 102 is a smartphone, this may be accomplished using, for example, a GSM module on the device. In one embodiment, portable fitness monitoring device 102 may also include local receiver 13 for receiving data from the position beacon system 200. In one embodiment, local receiver 13 may be a passive receiver. In some embodiments, local receiver 13 may comprise a transceiver adapted to receive and transmit data. In one exemplary embodiment, local receiver 13 may include an active or passive RFID tag capable of receiving a signal from the transmitter 204 of the mat 202 and transmitting data in reply to receiving the signal. In one embodiment, local receiver 13 may be included within GPS receiver 12. In another embodiment, local receiver 13 is discrete from GPS receiver 12. In one embodiment, as shown, for example, in FIG. 5, local receiver 13 may be embodied in a race chip 108 discrete from portable fitness monitoring device 102, but adapted to communicate with the device 102. In this manner, the position beacon system 200 may indirectly communicate location and/or timing data to the portable fitness monitoring device 102 (i.e., via the race chip 108). In one embodiment, race chip 108 may be mounted on the shoe of the participant 100 or inside the shoe (e.g., within a cavity in the sole of the shoe), for example.

As shown in FIG. 4, portable fitness monitoring device 102 may further include the processor 14, a visual and/or audible display 15, a memory 16, a power supply 17 such as a battery 17 (which may be exchangeable or rechargeable), a user input 18, and a speaker 19. Processor 14 is generally a unit that processes or controls computer readable media steps and commands associated with operation of portable fitness monitoring device 102 and interaction between portable fitness monitoring device 102, server 112, and position beacon system 200. As will be appreciated by those of ordinary skill in the art, the portable fitness monitoring device 102 components are operably connected to provide the functions and interactions necessary to provide the fitness monitoring methods described herein.

With continued reference to FIG. 4, in one embodiment, mat 202 (or tower 206) may further include a power supply 207, such as a battery 207 (which may be exchangeable or rechargeable), for powering the transmitter 204, and a processor 208 that processes or controls computer readable media steps and commands associated with operation of mat 202 and interaction between mat 202, server 112, and portable fitness monitoring device 102. In one embodiment, position beacon system 200 may further include memory, display, and user input components as will be appreciated. One or more of the components of system 200 may be provided on controller 210 so as to simplify maintenance and operation of the plurality of mats 202. As will be appreciated by those of ordinary skill in the art, the mat 202 components are operably connected to provide the functions and interactions necessary to provide the fitness monitoring methods described herein.

Figure 6:
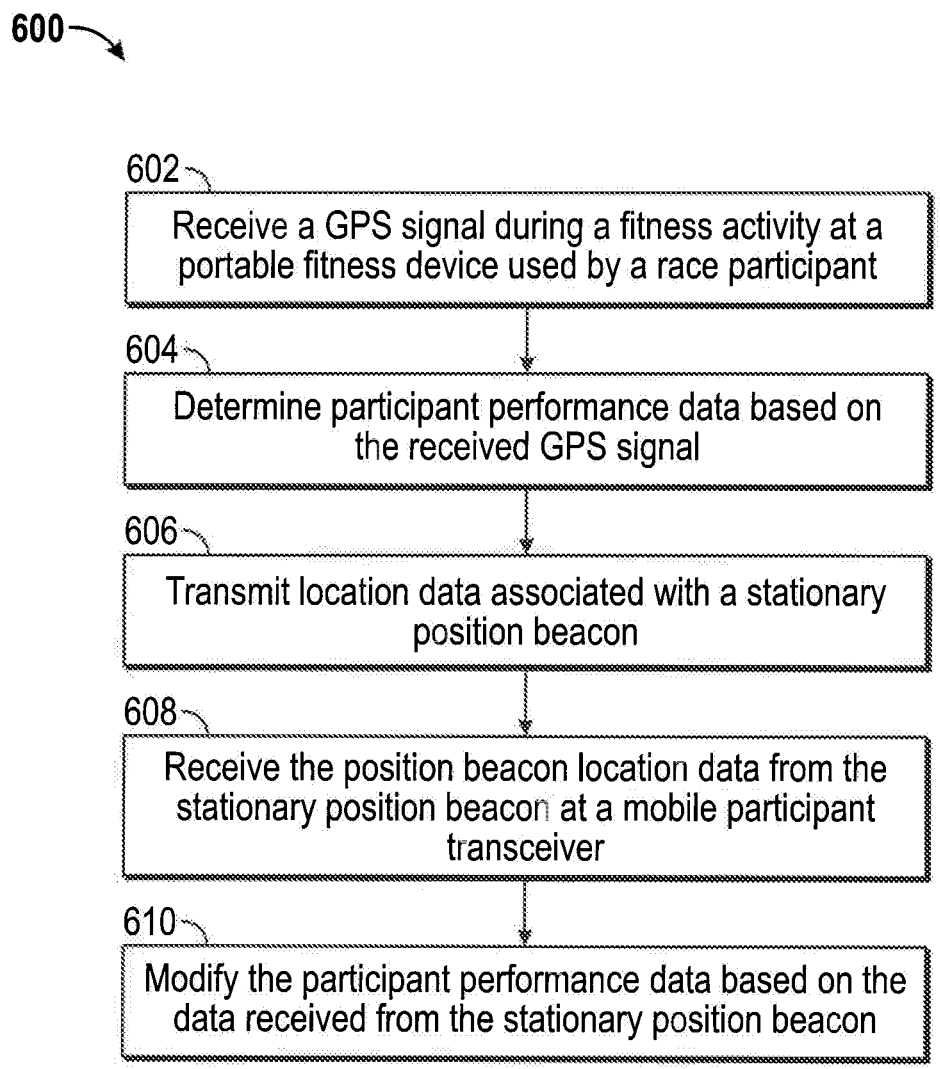
FIG. 6 is a flowchart depicting a method of monitoring the performance of a fitness activity participant according to an embodiment of the present invention.

The portable fitness monitoring device 102, the position beacon system 200, including the mat 202, and the fitness activity server 112 are adapted to interact with one another to provide the fitness monitoring methods of the present invention. FIG. 6 is a process flowchart for a method 600 of monitoring the performance of a participant 100 in a fitness activity according to an embodiment of the present invention. Method 600 may include at least steps 602, 604, 606, 608, and 610. Embodiments of system 10, as described herein, will be used to describe method 600, but the method is not intended to be limited thereto. Step 602 includes receiving a GPS signal during the fitness activity at the portable fitness monitoring device 102. In step 604, participant performance data, including one or more of the participant's current location, pace, speed, and distance traveled may be determined based upon the received GPS signal. In one embodiment, calculations may be performed by processor 14 on the portable fitness monitoring device 102 according to known techniques for calculating location, speed, pace, and distance, for example, from time-stamped GPS signals. In another embodiment, some or all of the calculations may be performed on fitness activity server 112.

In step 606, a unique time-stamped location signal is transmitted from a transmitter 204 of a stationary position beacon system mat 202. The signal may include the location of the mat 202 and the time at which the signal was transmitted. In step 608, the time-stamped location signal is received by a local transceiver 13 supported by the participant 100. The local transceiver 13 may be part of the portable fitness monitoring device 102, or may be a separate device in wireless communication with the beacon system transmitter 204.

In step 610, based on the time-stamped location data received from the stationary position beacon system mat 202, the system 10 modifies the participant performance data. For example, due to error tolerances or communication difficulties with GPS satellites 20 (e.g., when the participant 100 traverses under a bridge) the participant location determined based on the GPS signal received by the portable fitness monitoring device 102 may be imprecise. Because the exact location of the stationary position beacon system mat 202 is known, this location information may be used to determine a more precise location of the participant 100. In one embodiment, the location information received from the mat 202 may replace the location data determined based on the GPS signal alone. In another embodiment, the location data determined based on the GPS signal may be adjusted based on the location information received from the mat 202. For example, an average of the two sets of coordinates may be used as the modified participant location data. Because the participant location information is correlated with the time it was received, based on the time-stamped location signal received from the mat 202, other participant performance data including speed, pace, and distance traveled may be modified to provide more accurate data. Participant performance data previously determined during the fitness activity also may be updated accordingly.

In one embodiment, the updated participant performance data may be transmitted to server 112. In one embodiment, the updated participant performance data may be displayed to the participant 100 on the display 15 of the portable fitness monitoring device 102. The data may be continuously displayed during the fitness activity and also may be displayed after the fitness activity has been completed. In one embodiment, calculations necessary to modify the participant performance data may be performed by processor 14 on the portable fitness monitoring device 102 according to known techniques for calculating location, speed, pace, and distance, for example, from time-stamped GPS signals. In another embodiment, some or all of the calculations may be performed on fitness activity server 112. These calculations may be performed during and/or after the fitness activity.

Figure 7:
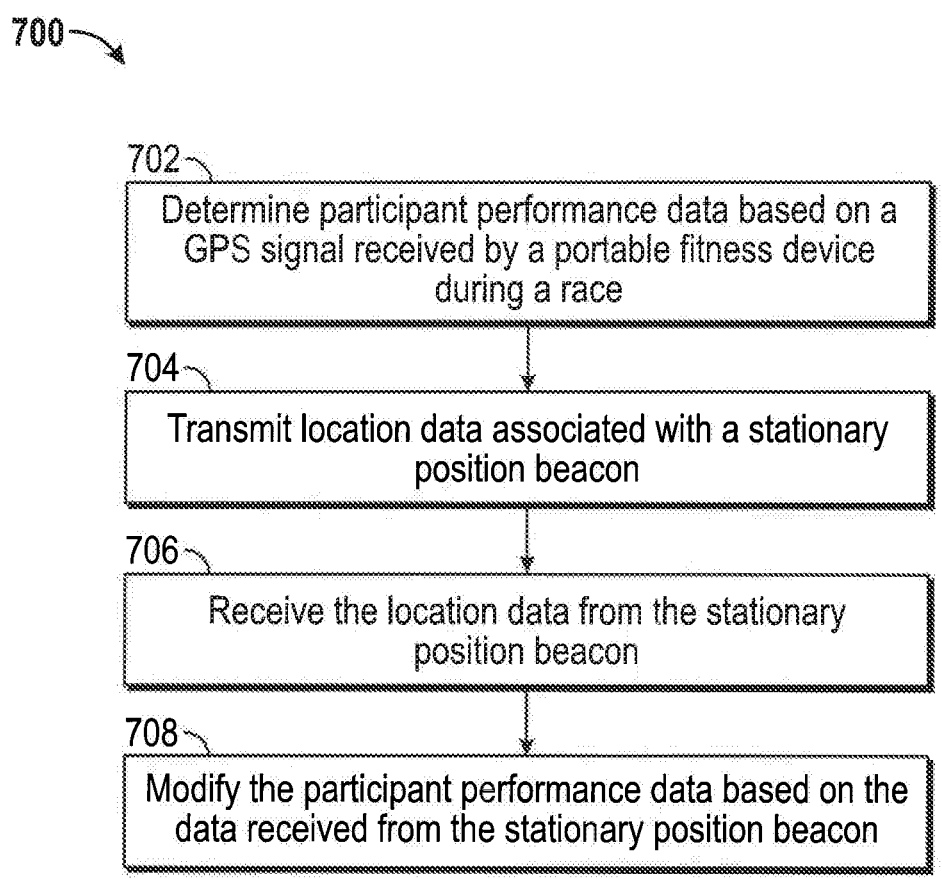
FIG. 7 is a flowchart depicting a method of monitoring the performance of a fitness activity participant according to an embodiment of the present invention.

FIG. 7 is a process flowchart for a method 700 of monitoring the performance of a participant 100 engaged in a competitive race having a predetermined route 120 according to an embodiment of the present invention. Method 700 may include at least steps 702, 704, 706, and 708. Embodiments of system 10, as described herein will be used to describe method 700, but the method is not intended to be limited thereto. In step 702, participant performance data, including the participant's current location, pace, speed, and distance traveled may be determined based upon a received GPS signal received by portable fitness monitoring device 102. In one embodiment, calculations may be performed by processor 14 on the portable fitness monitoring device 102 according to known techniques for calculating location, velocity, and bearing, for example, from time-stamped GPS signals. In another embodiment, some or all of the calculations may be performed on fitness activity server 112. In step 704, a unique time-stamped location signal is transmitted from a transmitter 204 of a stationary position beacon system mat 202. The mat 202 is placed at a predetermined location along the route 120. For example, a mat 202 may be placed at each mile marker of a marathon. The signal may include the location of the mat 202 and the time at which the signal was transmitted. In step 706, the time-stamped location signal is received by a local transceiver 13 supported by the participant 100. The local transceiver 13 may be part of the portable fitness monitoring device 102, or may be a separate device in wireless communication with the beacon system transmitter 204. In step 708, the participant performance data is modified based on the data received from the beacon system transmitter 204.

Figure 8:
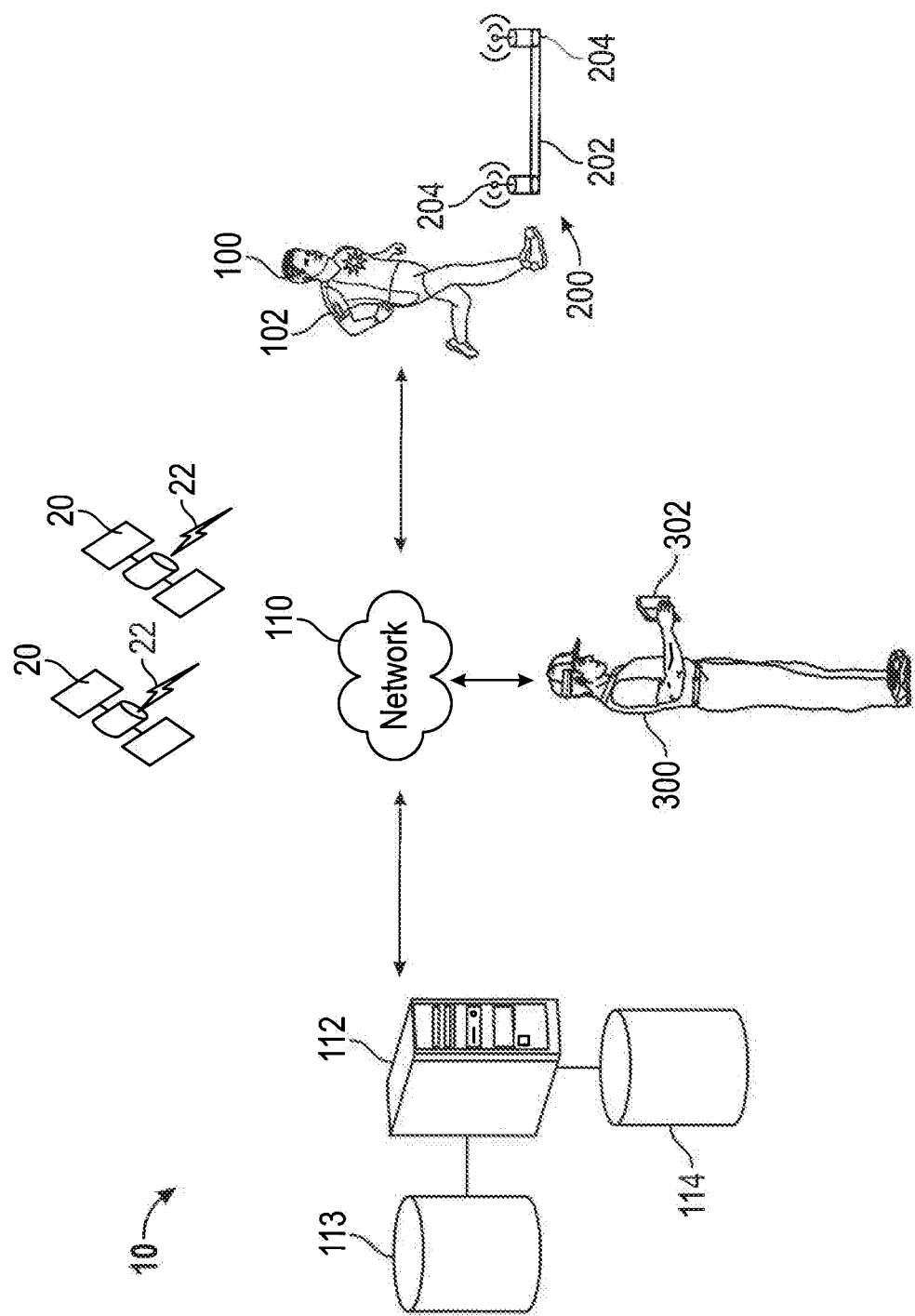
FIG. 8 is a schematic diagram of a fitness activity monitoring system in communication with a spectator according to an embodiment of the present invention.

With reference to FIG. 8, in one embodiment the portable fitness monitoring device 102, position beacon system 200, and fitness activity server 112 may be used to provide corrected participant performance data to a spectator 300 (on a spectator device 302, for example) who may be tracking the location of the participant 100 during the fitness activity. The spectator may include a coach, trainer, parent, supervisor, fan, aid station attendant, doctor, or other spectator of the fitness activity for which accurate participant location or other participant performance data may be useful. In one embodiment, another participant may be a "spectator" as they may wish to track the performance of the participant 100. It will be understood that a spectator may not be physically viewing the participant or the race. The spectator device 302 may be any suitable device, including, but not limited, to those described with respect to the portable fitness monitoring device 102. During the fitness activity, the system 10 may send an alert to the spectator 300 indicating that the participant is within a certain distance or time of reaching the spectator. During the fitness activity, the system may also send an alert to the participant 100 that the spectator 300 is within a certain distance or time of the participant. In this manner, embodiments of the present invention may provide real-time location awareness of the participant and/or spectator, and provide an enhanced participation or spectating experience of the fitness activity for individuals involved. For example, having been alerted that the participant they are tracking is approaching, an interested spectator may be informed to look for the participant and be ready to cheer on that individual or provide services (e.g., aid, water, equipment, etc.). Embodiments in which the location of the participant 100 is modified or corrected based on the location data from the position beacon system 200 may increase the likelihood of the participant and spectator being able to interact during the fitness activity. Accordingly, embodiments of the present invention may include the systems and methods, including the "Live Tracking" mobile application, described in co-owned U.S. patent application Ser. No. 13/335,545, entitled "Fitness Monitoring Systems and Methods" filed on Dec. 22, 2011, the disclosure of which is hereby incorporated by reference thereto in its entirety. As will be appreciated, a "Live Tracking" mobile application may be stored on or accessed by the portable fitness monitoring device 102 and/or the spectator device 302 and may be used to track the location of the participant 100 and/or spectator 200 during the fitness activity in real-time. For example, the "Live Tracking" mobile application may be downloaded to the devices from a known mobile application market.

In embodiments of the present invention, the portable fitness monitoring device 102 may be used in conjunction with, or separate from, the position beacon system 200. For example, in one embodiment, the location of the participant 100 may be determined based on the GPS signals received by the portable fitness monitoring device 102 only. This location data may then be used for real-time tracking of the participant 100 during the fitness activity and/or to see the route traversed by the participant 200, for example, when the participant is viewing a workout summary after a race. In one embodiment, the time-stamped location data transmitted by the race mat 202 may be the only data used to determine other participant performance data, such as pace, speed, and distance, for example. This performance data may be used, for example, to provide real-time performance data to the participant 200 and/or spectator 300, and coaching feedback to the participant 200. In other embodiments, as described above, corrected participant performance data may be determined using both the portable fitness monitoring device 102 and the position beacon system 200.

The server 112 may be, for example, a telecommunication server, a web server, or other similar types of database servers. In an embodiment, server 112 may have multiple processors and multiple shared or separate memory components such as, for example, one or more computing devices incorporated in a clustered computing environment or server farm. The computing process performed by the clustered computing environment, or server farm, can be carried out across multiple processors located at the same or different locations. In an embodiment, server 112 can be implemented on a single computing device.

In one embodiment, as shown in FIG. 8, the server 112 may include or be in communication with a fitness database 113 that may include an account of the participant 100 and/or spectator 300. For example, the fitness database 113 may include data storage according to embodiments described in U.S. Publication No. 2011/0082641, entitled "Methods and Computer Program Products for Providing Information About a User During a Physical Activity." The server 112 may also include or be in communication with a social network database 114 related to the participant 100 and/or spectator 300.

As will be appreciated, in an embodiment, the network 110 may be the internet. The internet is a worldwide collection of servers, routers, switches and transmission lines that employ the Internet Protocol (TCP/IP) to communicate data. In an alternate embodiment, the network may be a private network or intranet, such as, for example, a network dedicated to a particular fitness activity (e.g., the New York City Marathon). Other suitable communication networks may be used.

Alerts regarding the location of the participant 100 and/or spectator 300 may be sent to individuals, such as spectator 300, based on one or more predetermined alert parameters. Because the location of the participant 100 may be corrected based on the location data from the position beacon system 200, the alerts may be more accurate and the likelihood of the participant 100 and spectator 300 being able to interact during the fitness activity may be increased.

Alert parameters may be set by the participant 100 and/or the spectator 300 prior to or during the fitness activity. For example, in embodiments that include a "Live Tracking" mobile application, the application may provide an interface for defining the alert parameters. The alert parameters may be stored on the server 112 and accessed by the portable fitness monitoring device 102 and/or spectator device 302 over the network 110 (e.g., when a monitoring application is initiated), or may be stored on the devices themselves.

In one embodiment, the alert parameter may be distance based. For example, the spectator 300 may be alerted when the participant 100 is within a certain distance of their present location (e.g., 200 m). In one embodiment, the parameter may be time based and the spectator 300 may be alerted when the participant 100 is within a predetermined time of their present location. In one embodiment, this determination (i.e., estimated time of arrival) may be made based on the current location of the participant 100 and performance data received by the portable fitness monitoring device 102 from one or more receivers or sensors. For example, the estimated time of arrival may be based on the current pace of the participant 100. Because performance data, including the pace of the participant may be more accurately determined using data provided by mat 202, the alerts provided may be more accurate and the likelihood of the participant 100 and spectator 300 being able to interact during the fitness activity may be increased.

The alerts provided to the participant 100 and/or the spectator 300 may be visual, audible, tactile, or any combination thereof. To provide these alerts, the portable fitness monitoring device 102 and the spectator device 302 are adapted to convey information to the user in this manner. With reference to FIGS. 9 and 10, in one embodiment the portable fitness monitoring device 102 and the spectator device 302 include a display 15, 303 and a speaker 19, 305, respectively. To provide a tactile alert, the devices may include a vibrating element (not shown), for example, or other suitable tactile element.

Figure 11:
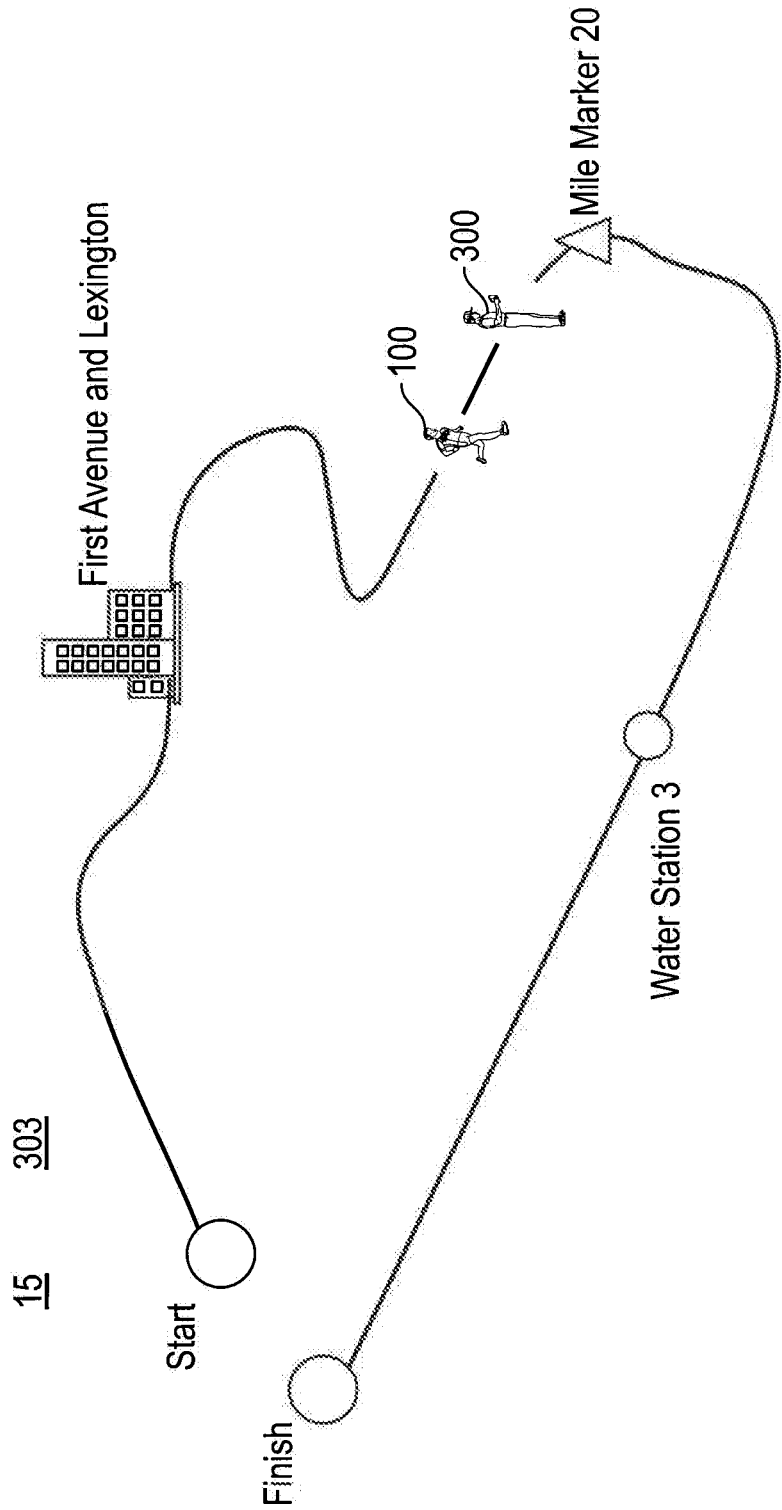
FIG. 11 is a schematic diagram of a fitness monitoring device display and/or a spectator device display depicting corrected participant performance data according to an embodiment of the present invention.

A visual alert may visually indicate to the participant 100 and/or spectator 300 the other's location, as shown, for example, in FIGS. 9, 10, and 11. In one embodiment, the visual alert may include information about the fitness activity, such as, a map of the route of the fitness activity and may include one or more graphical symbols. The graphical symbols may provide specific location information and may provide an indication of the relative location between the participant and the spectator. In one embodiment, graphical symbols indicate the location of the participant 100 and the spectator 300 along the route. In one embodiment, for example, the visual alert may provide a precise location of where the spectator 300 is standing. In this manner, in some embodiments, the visual alert may include a detailed map (e.g., a Google satellite map) of the predetermined route of the fitness activity and the spectator's location superimposed on the map.

As the participant 100 continues to traverse the route, the graphical symbol may move accordingly in real-time on the display. In one embodiment, the depiction of the participant 100 and the spectator 300 may comprise a photo or avatar of the individual. The visual alert may include graphical symbols of landmarks along the course, such as, start line, finish line, mile markers, water stations, or streets and landmarks specific to a particular event (e.g., First Avenue and Lexington during the New York City Marathon). The graphical symbols, including photos and avatars, may be stored on server 112, fitness database 113, and/or social network database 114, for example. As shown in FIGS. 9 and 10, the visual alert may include text indicating that the participant 100 (or spectator 200) is approaching. For example, the text may indicate that "The spectator is approaching in 30 seconds," "The spectator is at mile marker 20," "The participant is approaching in 200 m," "The spectator is located on the east side of the race course at First Avenue and Lexington," or "The participant just crossed the finish line." In one embodiment, the visual alert may include one or more advertisements related to the fitness activity or the location of the participant 100 or spectator 200, for example.

An audible alert may audibly indicate to the participant 100 and/or spectator 300 that the other is approaching through device speaker 19, 305 or headphones (not shown), for example. In one embodiment, the audible alert may include a standard message that "The spectator is at mile marker 20" or "The participant is approaching in 30 seconds." In one embodiment, the audible alert may be a customized, pre-recorded message. For example, spectator 300 may pre-record a message such as "Keep it up John! I'll see you in one mile!" which may provide additional motivation and encouragement to the participant. Alerts may be stored on the respective devices 102, 302 or on server 112.

A tactile alert may also indicate to the participant 100 and/or spectator 300 that the other is approaching. For example, a vibrating element of the spectator device 302 may vibrate when the participant 100 is within 200 m or within a specific time (e.g., 20 seconds).

In one embodiment, visual, audible, and/or tactile alerts may be sent to the participant 100 and/or spectator 300 at predetermined intervals, locations, distances, or times that are unrelated to the location of the other. For example, an audible message may be sent to the participant 100 every 5 miles or 30 minutes of a race or when the participant or spectator arrives at a particular mile marker or landmark, for example.

In some embodiments in which portable fitness monitoring device 102 is not phone enabled, the device is adapted to transmit GPS data over the network 110. For example, portable fitness monitoring device 102 may comprise a GPS-enabled watch adapted to transmit over the network 110 (e.g., using a GSM module). In some embodiments, portable fitness monitoring device 102 may not include a built-in GPS receiver 12. As such, participant performance data may be determined based solely on the time-stamped location data received by the device at each of the plurality of mats 202. For example, after the fitness activity a participant may upload the time-stamped location data from the plurality of mats 202 and the participant's location, speed, and pace may be determined along the predetermined route. In some embodiments, the location data based only on the GPS signal 22 from the satellites 20 may be used to provide location information to the spectator 300, and the performance data determined only using the position beacon system 200 data may be used to calculate participant performance data such as speed, pace, and distance.

In some embodiments, the methods described herein are adapted to be used with multiple participants 100. As will be appreciated, data transmitted to server 112 may include identifying information unique to each particular participant 200 so that the data may be properly stored and/or manipulated on server 112. In addition, a spectator 300 may track multiple participants 100.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A system for enhancing interaction between a participant engaged in a fitness activity and a spectator, the system comprising:
    stationary position beacons disposed along a route of the fitness activity;
    a portable fitness monitoring device configured to determine a location of the participant based on a received GPS signal and a signal received from the stationary position beacons; and
    a spectator device configured to determine a location of the spectator based on a received GPS signal,
    wherein the spectator device is configured to display a visual alert when a predetermined threshold relating to the participant is reached, wherein the predetermined threshold comprises a distance between the participant and the spectator, and wherein the visual alert comprises text that indicates the distance between the participant and the spectator.

2. The system of claim 1, wherein the visual alert comprises information about the fitness activity.

3. The system of claim 1, wherein the visual alert comprises a map of the route of the fitness activity.

4. The system of claim 1, wherein the visual alert comprises graphical symbols.

5. The system of claim 4, wherein the graphical symbols provide an indication of a relative location between the participant and the spectator.

6. The system of claim 4, wherein one of the graphical symbols indicates the location of the participant along the route.

7. The system of claim 6, wherein the graphical symbol for the participant moves in real time as the participant traverses the route.

8. The system of claim 4, wherein the graphical symbols comprise representations of landmarks along the route.

9. The system of claim 4, further comprising a server, the server storing the graphical symbols.

10. The system of claim 1, wherein the text indicates the location of the participant.

11. The system of claim 1, wherein the visual alert comprises an advertisement related to the fitness activity.

12. A method of enhancing interaction between a participant engaged in a fitness activity and a spectator, the method comprising:
    receiving a GPS signal during the fitness activity at a portable fitness device;
    receiving a signal from a stationary position beacon at the portable fitness device;
    determining a location of the participant based on the GPS signal and the signal from the stationary position beacon; and
    playing an audible alert based on the location of the participant, wherein the audible alert is played at predetermined intervals;
    wherein the audible alert comprises a pre-recorded message from the spectator.

13. The method of claim 12, wherein the audible alert comprises a message that the participant is within a predetermined metric of reaching the spectator.

14. The method of claim 13, wherein the predetermined metric comprises a distance.

15. The method of claim 13, wherein the predetermined metric comprises a time.

16. The method of claim 12, wherein the predetermined intervals comprise distance intervals.

17. The method of claim 12, wherein the predetermined intervals comprise time intervals.

18. The method of claim 12, wherein the audible alert is played when the participant arrives at a predetermined location.

19. A system for enhancing interaction between a participant engaged in a fitness activity and a spectator, the system comprising:
- stationary position beacons disposed along a route of the fitness activity;
- a portable fitness monitoring device configured to determine a location of the participant based on a received GPS signal and a signal received from the stationary position beacons; and
- a spectator device configured to determine a location of the spectator based on a received GPS signal,
- wherein the spectator device is configured to display a visual alert when a predetermined threshold relating to the participant is reached, wherein the predetermined threshold comprises a time until the participant reaches the spectator, and wherein the visual alert comprises text that indicates the time until the participant reaches the spectator.

20. The system of claim 19, wherein the visual alert comprises information about the fitness activity.

21. The system of claim 19, wherein the visual alert comprises a map of the route of the fitness activity.

22. A system for enhancing interaction between a participant engaged in a fitness activity and a spectator, the system comprising:
- stationary position beacons disposed along a route of the fitness activity;
- a portable fitness monitoring device configured to determine a location of the participant based on a received GPS signal and a signal received from the stationary position beacons; and
- a spectator device configured to determine a location of the spectator based on a received GPS signal,
- wherein the spectator device is configured to display a visual alert when a predetermined threshold relating to the participant is reached, wherein the visual alert comprises an advertisement related to the location of the spectator.

* * * * *